United States Patent [19]

Rees

[11] Patent Number: 4,654,748
[45] Date of Patent: Mar. 31, 1987

[54] CONDUCTIVE WRIST BAND
[75] Inventor: John J. M. Rees, Toccoa, Ga.
[73] Assignee: Coats & Clark, Inc., Stamford, Conn.
[21] Appl. No.: 794,755
[22] Filed: Nov. 4, 1985
[51] Int. Cl.[4] .................... D03D 15/02; D03D 15/08; H01R 4/66
[52] U.S. Cl. .................................. 361/220; 139/422; 139/425 R; 339/14 R
[58] Field of Search ............ 339/14 R; 361/212, 220, 361/223; 139/421, 422, 423, 425 R

[56] References Cited
U.S. PATENT DOCUMENTS

| | | | |
|---|---|---|---|
| 4,398,227 | 8/1983 | Christiansen et al. | 361/220 |
| 4,475,141 | 10/1984 | Antonevich | 361/220 |
| 4,567,094 | 1/1986 | Levin | 139/425 R X |
| 4,577,256 | 3/1986 | Breidegam | 361/220 |

Primary Examiner—Eugene F. Desmond
Attorney, Agent, or Firm—Burgess, Ryan & Wayne

[57] ABSTRACT

A conductive wrist band for dissipating electrostatic charges and having opposing transverse ends, includes a fabric; mechanical snap connectors coupled to the fabric ends for forming the fabric into a closed loop with an inside surface adapted to contact the body; an electrical connector coupled to the mechanical snap for providing a connection between the fabric and an electrical cable capable of connecting the conductive body strap to ground; and the fabric including a weft yarn extending between the opposing transverse ends and forming said inside surface and an opposite, outside surface; parallel rows of a substantially non-elastic, conductive yarn positioned in a sinusoidal manner on the inside surface of the weft yarn, parallel rows of a non-conductive elastic fiber positioned on the outside surface of the weft yarn in opposing relation to the conductive yarn, and a securing yarn for securing the conductive yarn and the elastic fiber to the weft yarn.

16 Claims, 6 Drawing Figures

CONDUCTIVE WRIST BAND

BACKGROUND OF THE INVENTION

The present invention relates generally to a conductive fabric and, more particularly, to a conductive wrist band employing such conductive fabric.

When handling static sensitive electronic components, such as integrated circuits and the like, there is a problem of damaging such components due to static electricity. One method of grounding such static electric charges has been to provide a conductive wrist strap about the wrist of the individual handling such components, which is in contact with the skin and is connected to ground by a wire connected to the wrist strap. As a result, the electrostatic charge accumulation on the individual is dissipated and the accumulation of additional electrostatic charge is prevented. Such conductive wrist straps are also provided in situations where the individual can be hurt, for example, in the proximity of an explosive or hazardous environment.

Some wrist bands are comprised of an extruded or fabric base matrix with a conductive plastic or film sewn into the structure. The conductive layer contacts the skin, and a metal snap connects the band to a ground cord that dissipates static electricity. Conventionally, these wrist bands use Velcro fasteners to secure the band to the wrist and are therefore stiff and uncomfortable. The same disadvantage generally results from metallic wrist bands, such as disclosed in U.S. Pat. Nos. 4,373,175 and 4,459,633. These latter devices also provide the disadvantage that the metallic material exists on the exterior surface thereof, and is therefore exposed to the electronic component or hazardous materials.

In order to make such wrist bands more comfortable for the user, it has been proposed in U.S. Pat. Nos. 4,398,277 and 4,475,141 to manufacture the conductive wrist bands from a fabric material.

In U.S. Pat. No. 4,475,141, the wrist band is made of an elastomeric fabric having a conductive thread stitched therein in a zig-zag manner. However, the conductive thread extends to the outer surface of the wrist band, whereby electrostatic charges may be transferred to the sensitive electronic components or harzardous materials.

U.S. Pat. No. 4,398,277 is an improvement thereover, since the conductive yarn is woven on one side only of the wrist band, while an insulative yarn is woven into the other side of the wrist band and in an interconnecting manner with the conductive yarn. Thus, the conductive yarn does not extend to the exterior surface of the wrist band. However, with this patent, the electrically conductive yarn is plaited with an elastic fiber. In addition, the insulative yarn contains an end having an insulative fiber plaited with an end having an elastomeric fiber. Because an elastomeric fiber is plaited with each of the insulative fiber and the conductive fiber, it is not easily handled in fabricating the wrist band because of the elastic nature of both yarns. Further, because the conductive yarn is plaited with an elastomeric fiber, the elastomeric fiber is in contact with the skin and may provide irritation thereof. Another problem with such arrangement is that the elastomeric fibers tend to close the fabric structure, thereby providing less aeration for the user. This latter problem is further enhanced by the fact that there are two distinct layers, one on top of each other, providing a double thickness, which is less comfortable and provides less aeration.

OBJECTS AND SUMMARY OF THE INVENTION

Accordingly, it is an object of the present invention to provide a conductive wrist band for assuring electrostatic discharge from an individual.

It is another object of the present invention to provide a conductive wrist band which is less irritable to the skin of the individual.

It is still another object of the present invention to provide a conductive wrist band made of a conductive fabric that can be easily and readily manufactured.

It is yet another object of the present invention to provide a conductive wrist band having increased aeration between the fibers.

It is a further object of the present invention to provide a conductive wrist band made of a single layer of material.

It is still a further object of the present invention to provide a conductive wrist band that produces less internal forces on the conductive yarn.

In accordance with an aspect of the present invention, a conductive fabric having opposing transverse ends, includes a weft yarn extending between the opposing transverse ends and forming opposite surfaces thereof; a substantially non-elastic, conductive yarn positioned on one surface of the weft yarn in a tortuous path; a non-conductive elastic fiber positioned on the opposite surface of the weft yarn; and at least one securing warp yarn for securing the conductive yarn and the elastic fiber to the weft yarn.

In accordance with another aspect of the present invention, a conductive body strap having opposing transverse ends, includes a fabric having a weft yarn extending between the opposing transverse ends and forming opposite surfaces thereof, a substantially non-elastic, conductive yarn positioned on one surface of the weft yarn in a tortuous path, a non-conductive elastic fiber positioned on the opposite surface of the weft yarn, and at least one securing warp yarn for securing the conductive yarn and the elastic fiber to the weft yarn; mechanical connection means coupled to the fabric for forming the fabric into a closed loop with an inside surface adapted to contact the body with the conductive yarn; and electrical connection means coupled to the conductive yarn for providing a connection between the conductive yarn and an electric cable capable of connecting the conductive body strap to ground.

The above and other, objects, features and advantages of the present invention will become readily apparent from the following detailed description thereof which is to be read in connection with the accompanying drawings.

DETAILED DESCRIPTION OF A PREFERRED EMBODIMENT

Figure 1:
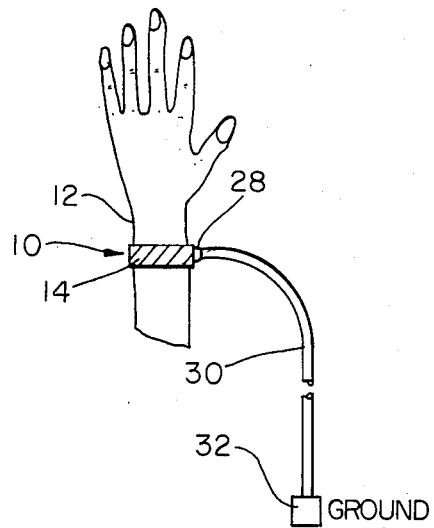
FIG. 1 is a schemetic view of a wrist band according to the present invention in an assembled and operative position.

Referring to the drawings in detail, and initially to FIG. 1 thereof, a wrist band 10 according to the present invention is adapted to fit over the wrist 12 of an individual handling sensitive electronic components or hazardous materials. Wrist band 10 is constructed from a fabric 14 which will be described in greater detail hereinafter.

Figure 5:
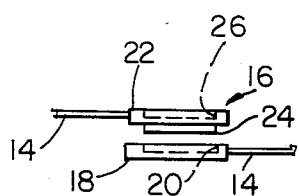
FIG. 5 is a side elevational view of the mechanical connecting portion for the wrist band of FIG. 1.
Figure 6:
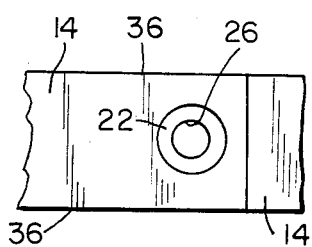
FIG. 6 is a top plan view of the mechanical connecting portion of FIG. 5.

Fabric 14 is generally made in an elongated section having mechanical connection means 16 secured to opposite ends thereof for forming fabric 14 into a wrist band. As an example, as shown in FIGS. 5 and 6, mechanical connection means 16 may include a first snap connector 18 connected to one end of fabric 14 and having a first snap recess 20, and a second snap connector 22 connected to the opposite end of fabric 14 and having a snap 24 which is snap fittingly engageable within recess 20 for securing the two ends together. The opposite side of second snap connector 22 includes a second snap recess 26 for receiving a snap 28 (FIG. 1) at the end of a grounding wire 30, the other end of which is connected to a source of ground 32.

Figure 2:
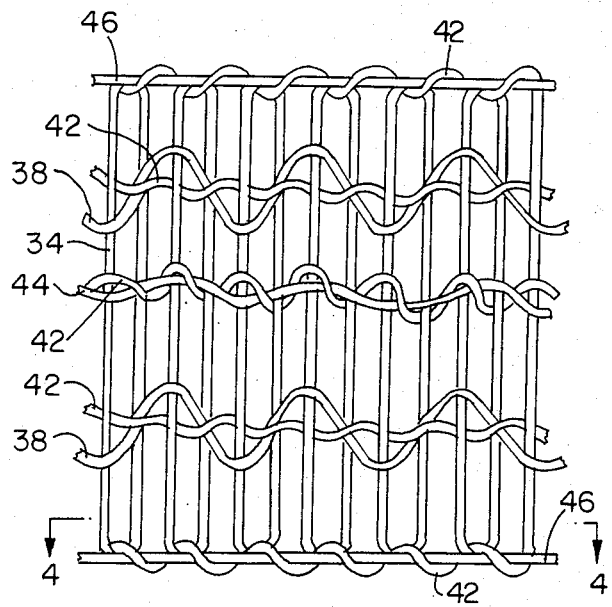
FIG. 2 is a bottom plan view of a portion of the fabric of the wrist band of FIG. 1.
Figure 3:
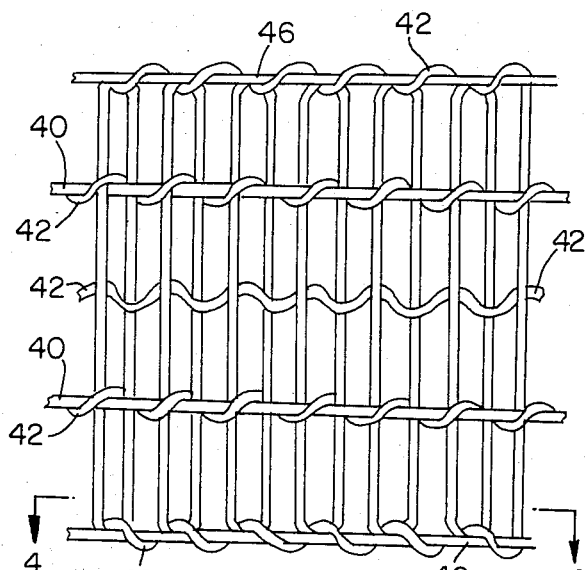
FIG. 3 is a top plan view of a portion of the fabric of the wrist band of FIG. 1.
Figure 4:
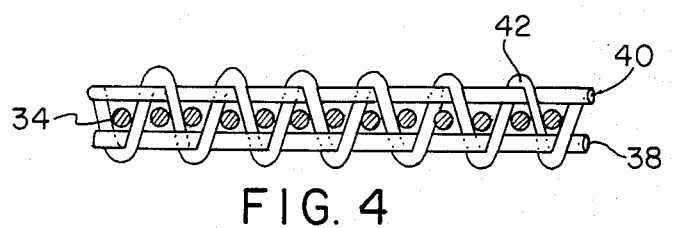
FIG. 4 is a cross-sectional view of the fabric of FIGS. 2 and 3, taken along line 4—4 thereof.

Referring now to FIGS. 2-4, a detailed description of fabric 14 will now be given. As shown, a weft yarn 34 is provided in a zig-zag manner between the widthwise or transverse ends 36 of fabric 14. Weft yarn 34 may, for example, be a polyester or nylon yarn, either textured or flat.

A substantially non-elastic, conductive yarn 38 is positioned on one surface of weft yarn 34, extending in a sinusoidal, zig-zag or like manner in the longitudinal direction of the fabric. Although two longitudinal rows of conductive yarn 38 are shown, it will be appreciated that any other suitable number can be provided. Conductive yarn 38 is a weft yarn which may, for example, be constituted by a plurality of metallic fibers, such as stainless steel, intertwined with a non-conductive strand, such as polyester filaments, to define a twisted composite, for example, Bekitex Bk conductive yarn, as described in U.S. Pat. No. 3,987,613. On the opposite, exterior surface of weft yarn 34, a non-conductive elastic fiber 40 is positioned in line with the zero or base axis of the sinusoidal curve of conductive yarn 38. Elastic fiber 40, for example, be a monofilament Lycra ® spandex 260 denier material.

A non-conductive, substantially non-elastic, securing yarn 42, such as 150 denier polyester yarn is provided for securing the conductive yarn 38 and elastic fiber 40 to weft yarn 34.

With this arrangement, conductive yarn 38 is positioned only on the inner surface of fabric 14 so that the aforementioned problems in U.S. Pat. No. 4,475,141 to not occur. In addition, since conductive yarn 38 is not made of an elastic material, problems in handling, that is, manufacturing, fabric 14 are minimized, and there is no elastic material in contact with the user's skin. Further, since elastic material is only provided in elastic fiber 40, there is a greater openness to the fabric when stretched, to provide greater aeration. Still further, it will be noted that only a single layer is effectively provided that is, weft yarn 34. Conductive yarn 38 and elastic fiber 40 merely are individual strands of material which minimize the bulkiness of the product. In addition, since conductive yarn 38 does not include any elastomeric fiber, there are less internal forces on the conductive yarn than would occur if combined with an elastomeric fiber, therefore increasing the longevity of the fabric.

As shown in FIGS. 2 and 3, in order to prevent the amount of stretch available in fabric 14, a longitudinally extending limiting yarn 44 is provided between rows of conductive yarn 38 and secured to weft yarn 34 by securing yarn 42. Limiting yarn 44 is preferably a polyester, or nylon or polypropylene (textured or flat) warp yarn having a sinusoidal zig-zag pattern with an amplitude much less than that of conductive yarn 38 so as to limit the amount of stretch of the fabric 14.

In addition, in order to provide greater longevity and stability to fabric 14, transverse ends 36 thereof are secured to an elastic fiber 46 by securing yarn 42. Elastic fiber 46 is substantially identical in makeup to elastic fiber 40.

The resultant conductive fabric 14 has abrasion resistance, laundering and comfort characteristics not achieved by previously known yarns.

EXAMPLE 1

The following conductive fabrics were manufactured in accordance with the present invention, as follows:

| Reference Numeral | Tape Width | ¾" | 1" |
|---|---|---|---|
| 42 | Front Warp | P-2P-P-2P-P-2P-P | P-P-P-P-P-P |
| 38, 44 | weft (1 Needle Trv.) | S-N-S-N-S | N-S-N-N—N-N-S-N |
| 34 | weft (Full Width Trv.) | Front 2P, Back 2P | Front 2P, Back 2P |
| 40, 46 | rear Warp | E-E—E—E-E | E-E-E-E—E-E-E-E |

Legend:
P = 2 × 150 Polyester, N = 240 Nylon, E = 2240 Coalesced Monofilament Lycra ® Spandex, S = Multifilament S.S.

Having described a specific preferred embodiment of the invention, it will be appreciated that the present invention is not limited to the specific preferred embodiment described, and that various changes and modifications may be effected therein by one of ordinary skill in the art without departing from the spirit and scope of the invention as defined by the appended claims.

What is claimed:

1. A conductive fabric having opposing transverse ends, comprising:
   a weft yarn extending between said opposing transverse ends and forming opposite surfaces thereof;
   a substantially non-elastic, conductive yarn positioned on one surface of said weft yarn in a tortuous path;
   a non-conductive elastic fiber positioned on the opposite surface of said weft yarn; and
   at least one securing warp yarn for securing said conductive yarn and said elastic fiber to said weft yarn.

2. A conductive fabric according to claim 1; wherein said tortuous path is a sinusoidal path.

3. A conductive fabric according to claim 1; further comprising a warp yarn extending in the direction of said conductive yarn in a tortuous path having an amplitude less than the amplitude of the tortuous path of said conductive yarn for limiting the fabric stretch.

4. A conductive fabric according to claim 3; wherein there is at least one parallel row of said conductive yarn positioned on one surface of said weft yarn, each in a tortuous path, and further comprising at least one row of warp yarn secured to said weft yarn substantially parallel to said conductive yarn and in a tortuous path having an amplitude less than the tortuous path of said conductive yarn, each said row of warp yarn extending adjacent to a row of said conductive yarn.

5. A conductive fabric according to claim 1; further comprising a non-conductive elastic fiber secured to said transverse ends of said fabric.

6. A conductive fabric according to claim 1; wherein said weft yarn is made of a material from the group consisting of polyester, nylon and polypropylene.

7. A conductive fabric according to claim 1; wherein said elastic fiber is a spandex elastic-like material.

8. A conductive body strap having opposing transverse ends, comprising:
 (a) a fabric having:
  (i) a weft yarn extending between said opposing transverse ends and forming opposite surfaces thereof;
  (ii) a substantially non-elastic, conductive yarn positioned on one surface of said weft yarn in a tortuous path;
  (iii) a non-conductive elastic fiber positioned on the opposite surface of said weft yarn; and
  (iv) at least one securing warp yarn for securing said conductive yarn and said elastic fiber to said weft yarn;
 (b) mechanical connection means coupled to said fabric for forming said fabric into a closed loop with an inside surface adapted to contact the body with said conductive yarn; and
 (c) electrical connection means coupled to said conductive yarn for providing a connection between said conductive yarn and an electrical cable capable of connecting said conductive body strap to ground.

9. A conductive body strap according to claim 8; wherein said tortuous path is a sinusoidal path.

10. A conductive body strap according to claim 8; further comprising a warp yarn extending in the direction of said conductive yarn in a tortuous path having an amplitude less than the amplitude of the tortuous path of said conductive yarn for limiting the fabric stretch.

11. A conductive body strap according to claim 10; wherein there is at least one parallel row of said conductive yarn positioned on one surface of said weft yarn, each in a tortuous path, and further comprising at least one row of warp yarn secured to said weft yarn substantially parallel to said conductive yarn and in a tortuous path having an amplitude less than the tortuous path of said conductive yarn, each said row of warp yarn extending adjacent to a row of said conductive yarn.

12. A conductive body strap according to claim 8; further comprising a non-conductive elastic fiber secured to said transverse ends of said fabric.

13. A conductive body strap according to claim 8; wherein said weft yarn is made of a material from the group consisting of polyester, nylon and polypropylene.

14. A conductive body strap according to claim 8; wherein said elastic fiber is a spandex elastic-like material.

15. A conductive body strap according to claim 8; wherein said mechanical connection means includes first snap means secured to one end of said fabric and second snap means secured to an opposite end of said fabric for releasably engaging said first snap means.

16. A conductive body stap according to claim 15; wherein said second snap means includes means for securing an electrical ground cable thereto.

* * * * *